United States Patent [19]

Basha et al.

[11] Patent Number: 5,292,900
[45] Date of Patent: Mar. 8, 1994

[54] O-SUBSTITUTED N-HYDROXYUREA DERIVATIVES

[75] Inventors: Anwer Basha, Lake Forest; Dee W. Brooks, Libertyville, both of Ill.

[73] Assignee: Abbott Laboratories, Abbott Park, Ill.

[21] Appl. No.: 992,389

[22] Filed: Dec. 18, 1992

[51] Int. Cl.$^5$ .................................. C07D 209/04
[52] U.S. Cl. .................................................. 549/419
[58] Field of Search .................................. 549/419

[56] References Cited

U.S. PATENT DOCUMENTS 4,873,259 10/1989 Summers, Jr. et al. ............... 514/443
5,112,848 5/1992 Brooks et al. ......................... 514/424

OTHER PUBLICATIONS

Reinheckel, et al., "Preparation . . . ", Angew. Chem. internatl. Edit./vol. 5 (1966)/No. 5, pp. 511–512.
T. W. Greene, "Protecting Groups in Organic Synthesis", John Wiley Publ. New York 1981 Chapter 2.
Chem. Abs. Service, 1972, CA77(11):71292x (Abstract of Frear, Phytochemisry 11(6) 1919–29, 1972).

*Primary Examiner*—Marianne M. Cintins
*Assistant Examiner*—Catherine S. Kilby Scalzo
*Attorney, Agent, or Firm*—Jerry F. Janssen

[57] ABSTRACT

The present invention provides compounds useful as intermediates for the preparation of 5-lipoxygenase inhibiting compounds. The intermediates of this invention have the structure

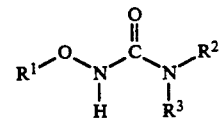

wherein $R^1$ is an O-protecting group selected from the group consisting of

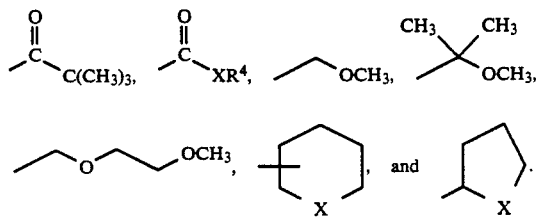

In the above, X is oxygen or sulfur.

1 Claim, No Drawings

O-SUBSTITUTED N-HYDROXYUREA DERIVATIVES

TECHNICAL FIELD

This invention relates to compounds which are useful as intermediates for the synthesis of organic compounds and a method of synthesis of organic compounds. More particularly, this invention concerns novel O-substituted-N-hydroxyurea intermediates and a method of synthesis of N-hydroxyurea-containing compounds having utility as leukotriene biosynthesis inhibitors.

BACKGROUND OF THE INVENTION

Furyl and benzo[b]thienyl substituted N-hydroxyureas, as exemplified by N-(1-fur-3-ylethyl)-N-hydroxyurea (U.S. Pat. No. 5,112,848), and N-(1-benzo[b]thien-2-ylethyl)-N-hydroxyurea (zileuton) (U.S. Pat. No. 4,873,259), are potent leukotriene biosynthesis inhibitors.

Numerous studies have implicated leukotrienes as important mediators of asthma, allergy, arthritis, psoriasis, and inflammation. Blocking the formation of leukotrienes with agents such as zileuton offers treatment for leukotriene mediated afflictions in man and animals.

SUMMARY OF THE INVENTION

In its principle embodiment, the present invention provides certain O-substituted-N-hydroxyurea derivatives which are useful as intermediates in the synthesis of leukotriene biosynthesis inhibitors and a process for the production of this important class of therapeutic agents.

The compounds of this invention have the structure I

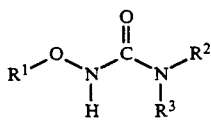

where $R^1$ is a protecting group selected from the group consisting of

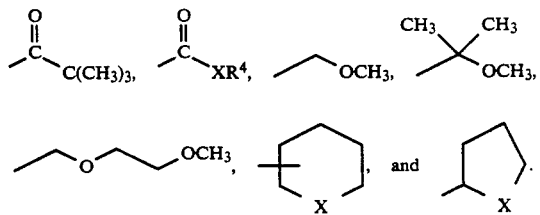

In the structures indicated above for $R^1$, X is oxygen or sulfur.

$R^2$ is selected from the group consisting of hydrogen, alkyl of from one to six carbon atoms, substituted or unsubstituted phenyl, substituted or unsubstituted phenylalkyl in which the alkyl portion contains from one to six carbon atoms; substituted or unsubstituted pyridyl, substituted or unsubstituted quinolyl, and substituted or unsubstituted thienyl where the substituents in each instance are selected from halogen, alkyl of from one to six carbon atoms, and alkoxy of from one to six carbon atoms. $R^3$ is hydrogen or alkyl of from one to six carbon atoms, and $R^4$ is alkyl of from one to four carbon atoms.

In another embodiment, the present invention provides a method of preparation of compounds which are useful as leukotriene biosynthesis inhibitors of structure II

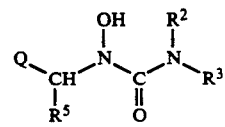

where $R^5$ is alkyl of from one to four carbon atoms, Q is selected from

and n is an integer from one to three.

The group Y is selected independently at each occurrence from (1) hydrogen, (2) halogen, (3) hydroxy, (4) cyano, (5) alkyl of from one to twelve carbon atoms, (6) alkenyl of from two to twelve carbon atoms, (7) alkoxy of from one to eight carbon atoms, (8) cycloalkyl of from three to eight carbon atoms, (9) thioalkyl in which the alkyl portion contains from one to eight carbon atoms, (10) aryl, (11) aryloxy, (12) aroyl, (13) arylalkyl in which the alkyl portion contains from one to twelve carbon atoms, (14) arylalkenyl, in which the alkenyl portion contains from two to twelve carbon atoms, (15) arylalkoxy in which the alkyl portion contains from one to twelve carbon atoms, (16) arylthioalkoxy in which the alkyl portion contains from one to twelve carbon atoms, and substituted derivatives of (17) aryl, (18) aryloxy, (19) aroyl, (20) arylalkyl in which the alkyl portion contains from one to twelve carbon atoms, (21) arylalkenyl, in which the alkenyl portion contains from two to twelve carbon atoms, (22) arylalkoxy in which the alkyl portion contains from one to twelve carbon atoms, (23) arylthioalkoxy in which the alkyl portion contain from one to twelve carbon atoms, where the substituents are selected from halogen, alkyl of from one to six carbon atoms, and alkoxy of from one to six carbon atoms.

The process of the present invention comprises the steps of a) reacting a compound of the structure

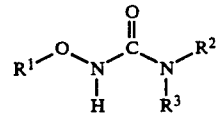

where $R^1$, $R^2$ and $R^3$ are as defined above with a base to obtain an anion of the structure;

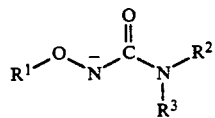

b) reacting said anion with a compound of the structure

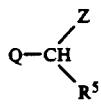

where Q and $R^5$ are as defined above and Z is selected from halogen, and $-OSO_2R^6$, where $R^6$ is selected from alkyl of from one to four phenyl or phenyl substituted with halogen, alkyl of from one to six carbon atoms and alkoxy of from one to six carbon atoms; and c) reacting the product of step b) with aqueous acid to produce an end-product of the structure

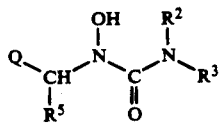

where Q, $R^2$, $R^3$, and $R^5$ are as defined above.

DETAILED DESCRIPTION OF THE INVENTION

DEFINITIONS OF TERMS

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "cycloalkyl" denotes a monovalent group derived from a monocyclic or bicyclic saturated carbocyclic ring compound by the removal of a single hydrogen atom. Examples include cyclopropyl, cyclobutyl, cycopentyl, cyclohexyl, bicyclo[2.2.1]heptanyl, and bicyclo[2.2.2]octanyl.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkyl" refers to an alkoxy group, as defined above, attached through an alkylene group to the parent molecular moiety.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocaron containing at least one carbon-carbon double bond. Examples of alkenylene include —CH=CH—, —CH2CH=CH—, —C(CH3)=CH—, —CH2CH=CHCH2—, and the like.

The term "alkanoyl" represents an alkyl group, as defined above, attached to the parent molecular moiety through a carbonyl group. Alkanoyl groups are exemplified by acetyl, propionyl, butanoyl and the like.

The term "aryl" is used herein to mean substituted or unsubstituted aromatic carbocyclic radicals and substituted or unsubstituted heterocyclic aromatic radicals including phenyl, pyridyl, quinolyl, and thienyl.

The term "arylalkyl" refers to an aryl group as defined above, attached to the parent molecular moiety through an alkylene group. Representative arylalkyl groups include phenylmethyl or benzyl, phenylethyl, phenylpropyl, 2-, 3-, and 4-pyridylmethyl, and the like.

Preferred Embodiments

Compounds contemplated as falling within the scope of the present invention include, but are not limited to O-pivaloyl-N-hydroxyurea,
O-tert-butoxycarbonyl-N-hydroxyurea,
O-tert-butylthiocarbonyl-N-hydroxyurea,
O-methoxycarbonyl-N-hydroxyurea,
O-methoxymethyl-N-hydroxyurea,
O-methoxyethylmethoxy-N-hydroxyurea,
O-dimethylmethoxymethyl-N-hydroxyurea,
O-(tetrahydropyran-2-yl)-N-hydroxyurea,
O-(tetrahydrothiopyran-2-yl)-N-hydroxyurea,
O-(tetrahydrofuran-2-yl)-N-hydroxyurea,
O-(tetrahydropyran-4-yl)-N-hydroxyurea,
O-(tetrahydrothiophen-2-yl)-N-hydroxyurea, Preferred compounds are those in which $R^2$ is hydrogen and $R^1$ is selected from the group consisting of

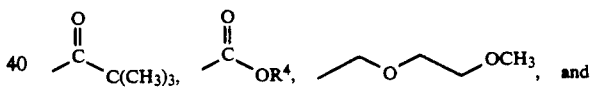

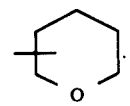

Particularly preferred compounds of the present invention are:
O-(tetrahydropyran-2-yl)-N-hydroxyurea,
O-tert-butoxycarbonyl-N-hydroxyurea,
O-pivaloyl-N-hydroxyurea,
O-methoxyethylmethoxy-N-hydroxyurea.

The most preferred compound of the present invention is
O-(tetrahydropyran-2-yl)-N-hydroxyurea.

When the compounds of this invention are used for the preparation of 5-lipoxygenase inhibitors in accordance with the process embodiment of the invention, the first step consists of deprotonation of a starting material of the formula

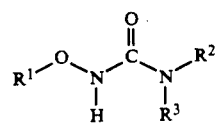

where $R^1$, $R^2$ and $R^3$ are as previously defined. These starting materials are readily obtained by reaction of the N-hydroxyurea, N-hydroxy-N'-alkylurea or N-hydroxy-N',N'-dialkylurea with the desired O-protecting group. Methods for this step are described in Chapter 2, "Protection for Hydroxyl Groups," by T. W. Greene, "Protecting Groups in Organic Synthesis," John Wiley, New York, 1981.

The deprotonation step is carried out in an aprotic organic solvent such as dimethylsulfoxide, tetrahydrofuran, acetone, acetonitrile or the like in the presence of a base such as diisopropylamine, lithium diisopropylamine (LDA), sodium hydride, sodium or potassium carbonate, and the like. The preferred base and solvent systems for this step are sodium or potassium carbonate in acetone. The reaction is carried out at a temperature generally ranging between about −10° C. to about room temperature, with a preferred temperature of about 0° C. The reaction is allowed to proceed for about one-half to one hour.

Following deprotonation of the starting O-protected N-hydroxyurea, the second step is carried out in the same reaction vessel by slow addition of a compound of the structure

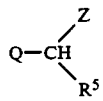

where Q, $R^5$ and Z are as previously defined. Following addition of the reagent, the reaction is allowed to proceed at room temperature to completion, generally for about three to six hours.

In the final step of the process, the O-protecting group is removed by hydrolysis by adding aqueous acid cautiously to the reaction mixture. Any aqueous inorganic acid suffices for this hydrolysis step, with 1N to 6N aqueous hydrochloric acid being typical.

Following hydrolysis, the final product of the reaction is separated from the aqueous reaction mixture by extraction with an organic solvent such as diethyl ether, drying over a dessicant such as magnesium sulfate, and recovery by evaporation of the extraction solvent.

The foregoing may be better understood by the following Examples, which are presented for the purpose of illustration and not intended to limit the scope of the inventive concept.

EXAMPLE 1

Preparation of O-(tetrahydropyran-2-yl)-N-hydroxyurea.

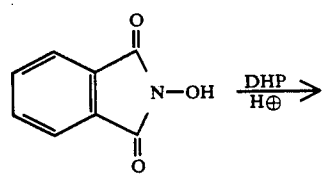

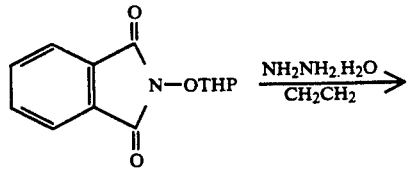

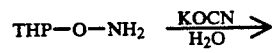

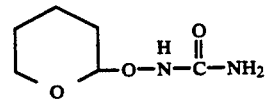

Step 1. N-(O-tetrahydro-4H-pyran-2-yl)hydroxyphthalimide.

A solution of N-hydroxyphthalimide (100 g, 0.613 mole), 3,4-dihydro-2H-pyran (56 ml, 0.613 mole), and phosphorus oxychloride (3 ml) in methylene chloride (500 ml) was stirred at ambient temperature for 19 hours. The reaction mixture was washed with saturated aqueous sodium carbonate and the organic layer was separated and passed through a thick pad of silica gel. Evaporation of the solvent in vacuo afforded 139 g (92%) of N-(O-tetrahydro-4H-pyran-2-yl)hydroxyphthalimide. mp 122°-23° (lit. mp 123° C., Angew. Chem. Int. Ed. 1966, 5, 511).

Step 2. O-(tetrahydro-4H-pyran-2-yl)hydroxylamine.

A solution of N-(O-tetrahydro-4H-pyran-2-yl)hydroxyphthalimide (156.6 g; 0.634 mol), prepared as in step 1, in methylene chloride (21), was treated with hydrazine hydrate (34 ml, 0.66 mol) and heated at reflux for 20 hours. The reaction mixture was filtered and the precipitate was washed with 20% tetrahydrofuran in pentane. Evaporation of the solvent in vacuo and distillation afforded O-(tetrahydro-4H-pyran-2-yl)hydroxylamine (50.4 g, 67%), b.p. 45°–50° C./0.2 torr.

Step 3. O-(tetrahydropyran-2-yl)-N-hydroxyurea.

O-(tetrahydro-4H-pyran-2-yl)hydroxylamine (10 g, 85.5 mmol), prepared as in step 2, and KOCN (13.8 g, 171 mmol) were combined in 10 mL water and 3M HCl (30 ml) was added slowly until effervescence ceased (pH 5.5). After stirring at ambient temperature for 0.5 hours, ethanol was added and the solvents were evaporated. The residue was extracted with acetone. Evaporation of the solvent and recrystallization from acetone provided O-(tetrahydropyran-2-yl)-N-hydroxyurea (11.2 g; 82%). mp 138°–139° C. $^1$H NMR (DMSO-d6) δ 1.4–1.5 (3H, m), 1.6–1.7 (3H, m), 3.4–3.6(1H, m), 3.8–3.9 (1H, m), 4.65–4.7 (1H, t, J=3 Hz), 6.2–6.35 (2H, br s), 8.95 (1H, s). MS 161 (M+H)+, 178 (M+NH4)+. Analysis calc. for $C_6H_{12}N_2O_3$: C, 45.0; H, 7.5; N, 17.5. Found: C, 44.76; H, 7.38; N, 17.41.

Alternatively, a solution of O-(tetrahydro-4H-pyran-2-yl)hydroxylamine (3.79 g, 31.9 mmol), prepared as in step 2, in dichloromethane was treated with trimethylsilylisocyanate (5 g) and heated at reflux for 2 hours, then stirred at 30° C. for 17 hours. Evaporation of the solvent provided O-(tetrahydropyran-2-yl)-N-hydroxyurea (3 g, 60%).

EXAMPLE 2

Preparation of O-methoxyethylmethoxy-N-hydroxyurea

The desired product is prepared according to the method of Example 1, except substituting methoxyethoxymethyl chloride and diisopropylethylamine for 3,4-dihydro-2H-pyran and phosphorus oxychloride.

EXAMPLE 3

Preparation of O-tert-butoxycarbonyl-N-hydroxyurea

To a suspension of hydroxyurea (3 g, 39.5 mmol) and triethylamine (2 mL) in acetonitrile (50 mL) was added di-tert-butyl dicarbonate (BOC$_2$O, 8.6 g, 39.5 mmol) and the mixture was stirred at ambient temperature for 1 hour. The solvent was evaporated and the residue was purified by filtration through silica gel eluting with a gradient of dichloromethane to 4% methanol in dichloromethane to afford O-tert-butoxycarbonyl-N-hydroxyurea (5 g, 72%), after evaporation of the solvent.

$^1$H NMR (DMSO-d6) δ 1.45 (9H, s), 6.45 (2H, br s), 9.6 (1H, s). MS 194 (M+NH$_4$)$^+$.

EXAMPLE 4

Preparation of O-pivaloyl-N-hydroxyurea

The desired product is prepared According to the method of Example 5, except substituting pivaloyl chloride for BOC$_2$O.

EXAMPLE 5

Preparation of N-(1-benzo[b]thien-2ylethyl)-N-hydroxyurea (zileuton)

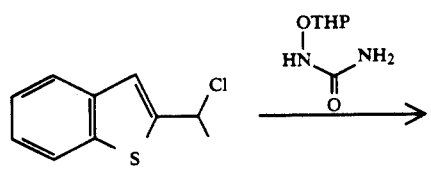

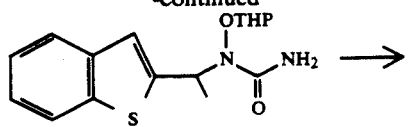

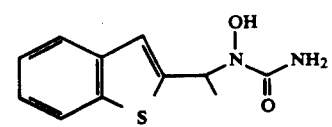

Step 1. N-(1-benzo[b]thien-2ylethyl)-O-(tetrahydropyran-2yl)-N-hydroxyurea.

A solution of O-(tetrahydropyran-2yl)-N-hydroxyurea (0.896 g, 5.6 mmol), prepared as in Example 1, in DMF (2 mL) was cooled in an ice-water bath and NaH (0.25 g, 60% in mineral oil, 6.2 mmol) was added. The reaction mixture was stirred for 30 min and then allowed to warm to ambient temperature. A solution of 1-(benzo[b]thien-2-yl)-1-chloroethane (1 g), prepared as described in U.S. Pat. No. 4,873,259, in DMF (2 mL) was added and the mixture was stired at ambient temperature for 6 hours. Water (15 mL) was added and the mixture was extracted with ethyl acetate. The organic extract was dried over MgSO$_4$ and the solvent was removed under reduced pressure. Chromatography on silica gel (1:4 CH$_2$Cl$_2$, pentane) provided N-(1-benzo[b]thien-2ylethyl)-O-(tetrahydropyran-2-yl)-N-hydroxyurea (890 mg, 50%). Alternatively, DMSO, dichloroethane or THF can be substituted for DMF, and K$_2$CO$_3$ or Na$_2$CO$_3$ can be substituted for NaH.

Step 2. N-(1-benzo[b]thien-2ylethyl)-N-hydroxyurea.
N-(1-benzo[b]thien-2ylethyl)-O-(tetrahydropyran-2-yl)-N-hydroxyurea (250 mg, 0.78 mmol), prepared as in step 1, was dissolved in a mixture of ethanol (10 mL) and 6N HCl (1 mL) and refluxed for 1 hour. The solvent was removed under reduced pressure and the residue was recrystallized from CH$_2$Cl$_2$ to provide a crystalline product (170 mg, 92% yield), which was identical to an authentic sample of N-(1-benzo[b]thien-2-ylethyl)-N-hydroxyurea prepared by a literature route (U.S. Pat. No. 4,873,259, Oct. 10, 1989).

We claim:
1. The compound having the name O-(tetrahydropyran-2-yl)-N-hydroxyurea.

* * * * *